(12) United States Patent
Storer et al.

(10) Patent No.: US 6,200,319 B1
(45) Date of Patent: Mar. 13, 2001

(54) SURGICAL TREPHINE

(75) Inventors: John Andrew Storer, Bayeux; Jean-Claude Bachelier, Bieville/Beuville, both of (FR)

(73) Assignee: Benoist Girard SAS (FR)

( * ) Notice: Subject to any disclaimer, the term of this patent is extended or adjusted under 35 U.S.C. 154(b) by 0 days.

(21) Appl. No.: 09/416,913

(22) Filed: Oct. 13, 1999

(30) Foreign Application Priority Data

Oct. 23, 1998 (GB) .................................................. 9823305

(51) Int. Cl.[7] .................................................. A61B 17/16
(52) U.S. Cl. .............................................................. 606/79
(58) Field of Search ............................... 606/79, 80, 86, 606/93, 94, 95, 105

(56) References Cited

U.S. PATENT DOCUMENTS

| 4,751,922 | 6/1988 | DiPietropolo | 128/92 |
|---|---|---|---|
| 4,895,146 | 1/1990 | Draenert | 606/79 |
| 5,122,134 | 6/1992 | Borzone et al. | 606/80 |
| 5,192,283 | 3/1993 | Ling et al. | 606/93 |
| 5,470,336 | 11/1995 | Ling et al. | 606/105 |
| 5,632,747 | 5/1997 | Scarborough et al. | 606/79 |
| 5,683,395 | 11/1997 | Mikhail | 606/86 |
| 5,718,707 | 2/1998 | Mikhail | 606/94 |
| 5,755,720 | 5/1998 | Mikhail | 606/94 |
| 5,788,704 | 8/1998 | Timperley | 606/95 |
| 5,908,423 | 6/1999 | Kashuba et al. | 606/80 |
| 5,925,051 | 7/1999 | Mikhail | 606/94 |
| 5,989,260 | * 11/1999 | Yao | 606/102 |
| 6,007,496 | * 12/1999 | Brannon | 600/565 |

FOREIGN PATENT DOCUMENTS

| 0 408 109 A1 | 7/1990 | (EP) . |
|---|---|---|
| 2 749 154 | 12/1997 | (FR) . |
| 2170127 | 7/1986 | (GB) . |

* cited by examiner

*Primary Examiner*—Michael Buiz
*Assistant Examiner*—Vy Q. Bui
(74) *Attorney, Agent, or Firm*—Lerner, David, Littenberg, Krumholz & Mentlik, LLP

(57) ABSTRACT

A surgical trephine is adapted for boring an opening in tamped bone chips and includes a hollow elongate body portion having an internal bore and the distal end of which has an annular cutting rim. A piston is located in the bore with a piston surface facing towards the cutting rim and a tool for moving the piston in the bore. With this device an elongate cavity can be cut in the bone chips. The debris from the cutting the bore enters the distal end of the internal bore and slowly pushes the piston up the bore away from the distal end. When the hollow elongate body portion is withdrawn from the cavity, the chips can then be easily dislodged from the bore by displacing the piston.

20 Claims, 3 Drawing Sheets

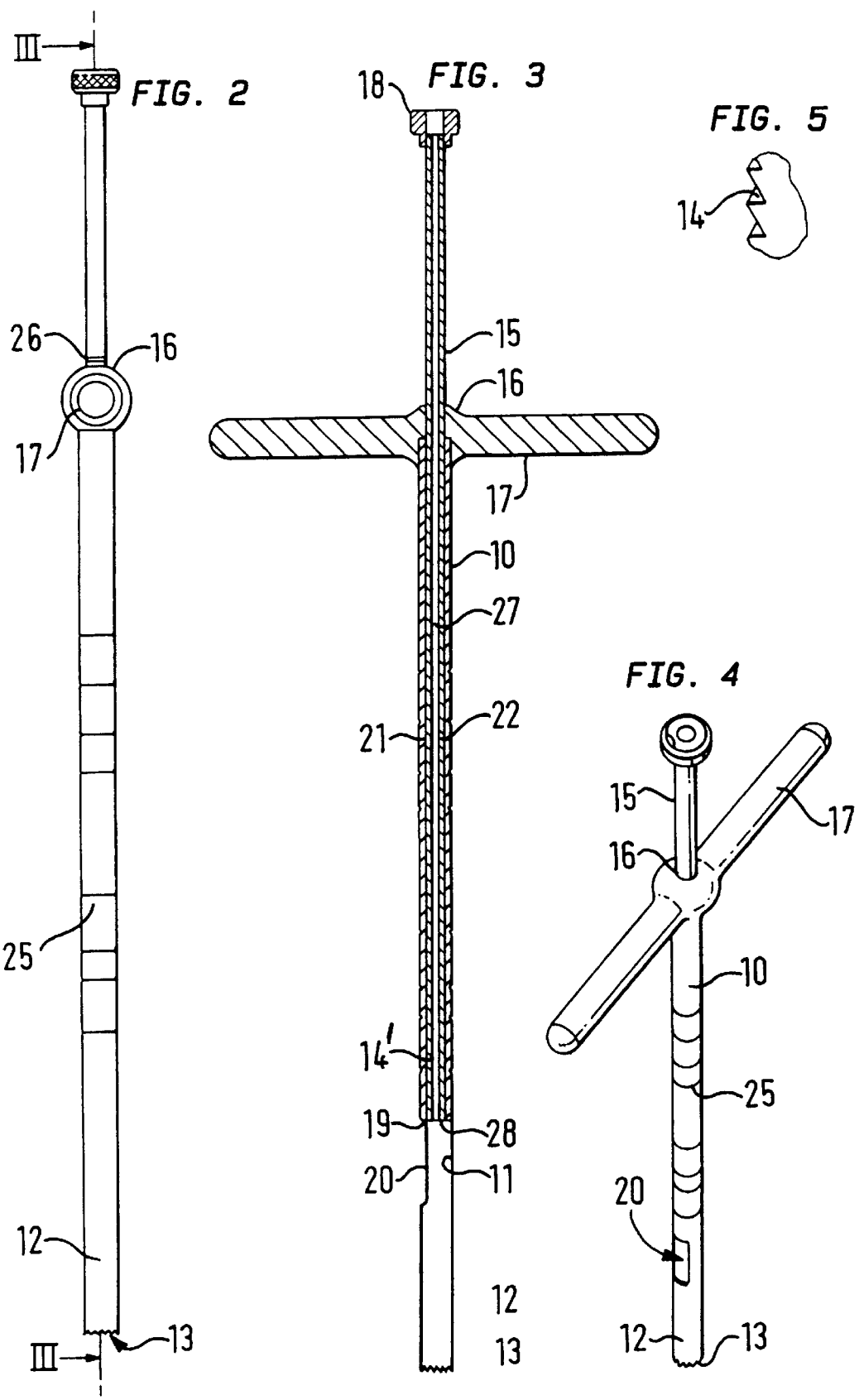

SURGICAL TREPHINE

BACKGROUND OF THE INVENTION

1. Field of the Invention

This invention relates to a surgical trephine adapted for boring an opening in tamped bone chips.

2. Description of the Prior Art

Modern surgical techniques, especially as applied to hip prostheses, sometimes require a prosthetic device with an elongated stem. These devices are used when not only are there problems with the hip joint but where there is also the possibility of fracturing in the length of the femur. The addition of a standard length prosthesis stem into such a femur can sometimes create further problems and for this reason a stem of much longer length is employed. The distal portion of such stems is usually parallel because of the extended length and the narrowing of the femur and its intramedullary canal.

In modern techniques bone chips can be employed to line the intramedullary canal and these chips are first tamped into position, for example as described and shown in the Applicants U.S. Pat. No. 5,788,704. This patent shows a method and apparatus for implanting a prosthesis in which a bone cavity is filled with bone chips which are compressed.

When such a technique is used for long prosthesis stems there are difficulties in shaping the distal end of the cavity due, not only to the long length, but also to the possibilities of causing further compression of the bone chips and thus tending to expand the filling and create fractures in the bone structure.

The present invention is intended to provide an instrument which can be used for cutting the required cavity into the bone chips in operations of the kind described above, although it can be used for any cavity in which bone chips are used and a substantially parallel cavity is required.

SUMMARY OF THE INVENTION

According to the present invention a surgical trephine adapted for boring an opening in tamped bone chips includes a hollow elongate body portion having an internal bore and the distal end of which has an annular cutting rim, a piston located in the bore with a piston surface facing towards said cutting rim and means for moving the piston in the bore.

With this device an elongate cavity can be cut in the bone chip, with the debris from the cutting entering the distal end of the internal bore and slowly pushing the piston up the bore away from the distal end. When the body portion is withdrawn from the cavity, the chips can then be easily dislodged from the bore by displacing the piston.

The body portion may include an aperture in the wall passing into the bore at a point spaced away from the distal end of the instrument to facilitate cleaning after operation. The action of the instrument when used by the surgeon can be back and forth or with a continuous rotation or with an up and down motion in the form of a pile driver.

Preferably an extension or extended portion of the piston projects beyond the proximal end of the body portion and a stop can be provided for limiting the movement of the piston up said bore and away from the distal end to a position adjacent the proximal end of the aperture.

Preferably the annular cutting rim is provided with cutting teeth although, in certain circumstances, merely a sharpened edge may be required.

The proximal end of the extended portion of the piston or an extension thereof can be provided with a removable stop to limit the movement of the piston in a distal direction. This stop can be removed so that the device can be completely dismantled for cleaning but when it is in position it locates the piston in the bore and prevents the piston dropping through the main body.

Preferably the hollow elongate body portion is provided with an operating handle which can be in the form of a T-piece.

The hollow elongate body portion can also be provided with a depth gauge and means such as a reference mark can be provided on the extended portion of the piston, or extension thereof, to provide a position indicator.

If desired the proximal end of the extended portion of the piston, or an extension thereof, can be provided with a coupling for attaching a power source so that the device can be operated by a power device.

The piston can be provided with a cannulation to accept a guide wire so that the trephine can be used as one of a series of operations when carrying out the preparation of the bone for implantation.

BRIEF DESCRIPTION OF THE DRAWINGS

The invention can be performed in various ways but one embodiment will now be described by way of example and with reference to the accompanying drawings, in which:

FIG. 2 is a side elevation of a surgical trephine according to the present invention;

FIG. 3 is a cross-sectional front elevation of the device shown in FIG. 2 on the lines III—III;

FIG. 4 is an isometric view of the trephine according to the invention;

FIG. 5 is an enlarged view of the teeth used on the annular cutting rim of the device according to the invention;

DESCRIPTION OF THE PREFERRED EMBODIMENTS

Figure 1:
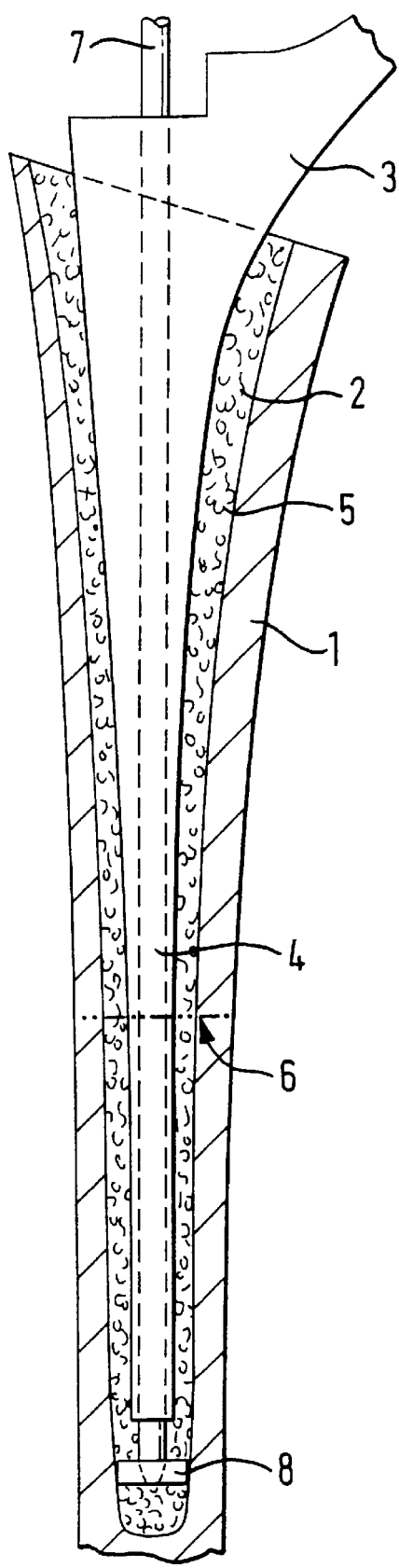
FIG. 1 is a diagrammatic illustration of a typical phantom or trial for a prosthesis with a long stem impacted into bone chips in a femur.
Figure 6:
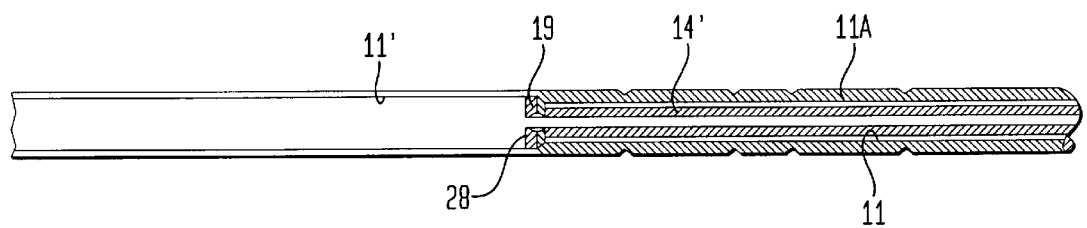
FIG. 6 is a cross-sectional view of the distal end of the trephine showing the piston in the trephine bore.

In FIG. 1 a femur 1 is shown in which the intramedullary canal has been treated to provide a cavity 2 into which a prosthesis with a long stem is intended to be inserted. In FIG. 1 a phantom or trial prosthesis 3 with a long stem 4 is shown which will eventually be removed and replaced by the surgical prosthesis. This technique is described and shown in U.S. Pat. No. 5,788,704, the teachings of which are incorporated herein by reference. When the cavity 2 has been prepared it is filled with bone chips 5 and these are tamped and compressed. When a long stem is to be used however there are difficulties in tamping the bone chips against the sides of the cavity 2 by the usual techniques but the present invention allows the distal end of the cavity to be completely filled with bone chips up to a level indicated by reference numeral 6.

When the bone cavity is being prepared a guide wire 7 is placed in position, usually held by a retaining plug 8, and this guide wire is used, in well known manner, to guide and accurately locate the various components which are used during the operation. The guide wire is, of course, placed in position before the bone chips are inserted. When a phantom technique is employed the phantom 3 is withdrawn, the cavity within the bone chips is lined with cement and the surgical prosthesis subsequently inserted with or without the use of a guide wire.

The present invention provides a trephine which can be used to cut out the tamped and compressed bone fragments beneath the level 6 and comprises a hollow elongate body portion which has an internal bore 11 and the distal end 12 of which has an annular cutting rim 13. The cutting rim can be provided with teeth 14, as shown in FIG. 5.

Located in the bore 11 is an elongate piston 14' which has an extension 15 which projects from the proximal end 16 of the main body 10. In the construction shown in the drawings the main body 10 is extended by a t-shaped cross-piece 17 which acts an operating handle.

The proximal end of the extension 15 is provided with a knurled nut 18 which is shaped to allow easy removal and is adapted to receive an appropriate operating attachment from a power tool. As the nut 18 is screw threaded onto the end of the extension 15 it can be readily removed by hand but it acts as a stop to prevent the piston 14' passing completely through the main body portion 10.

The distal end of the piston 14' is enlarged at 19 and the diameter of the bore 11 is also enlarged at its distal end 11 to accommodate the enlarged portion 19 on the piston. An aperture 20 is provided in the wall of the bore 11 and the enlarged portion of the bore ends at the proximal end of this aperture. Thus, the piston 14' can move towards the distal end of the bore 11 until it emerges from the distal end thereof. Further movement is however restricted by the stop 18. In the other proximal direction the piston can move up the bore 11 until it reaches the position shown in the drawings and where the enlarged part of the piston 19 meets the thicker wall 11a of the upper part of the bore 11. At all times the piston is guided by its wall 21 operating in the narrower part 22 of the bore 11 and the enlarged portion of the piston 19 therefore limits the movement of the piston up the bore and away from the annular cutting rim 13 to a position adjacent the proximal end of aperture 20.

The outer surface of the elongate body portion is provided with a depth gauge in the form of appropriate markings indicated by reference numeral 25 and the piston extension 15 carries a position indicator 26 which indicates when the piston 19 has reached the upper end of the aperture 20. The piston 14 and extension 15 are provided with means to accept a guide wire in the form of a guide bore 27.

In operation the trephine is fed down a guide wire, for example similar to that shown in FIG. 1 and indicated by reference numeral 7, and a backwards and forwards or rotary movement is applied by the operating handle 17 to cause the cutting rim 13 to cut into the bone chips, the chips which have been cut away passing up the bore 11 and pushing the face 28 of the piston in front of them. The precise depth of the trephine within the bone can be seen from the depth gauge 25. Frequent removal of the device will enable the surgeon to see how far the bone chips have passed up the bore 11 but the position indicator 26 will immediately make him aware if the lower end of the bore 11 has become completely filled. The device is now removed from the cavity and the bone chips can be easily expelled by pushing the piston downwardly so that the chips are expelled through the opening 20 or through the open distal end. Cutting can now be resumed until the required depth, as indicated on the depth gauge 25, is achieved to thus provide an opening which is suitable to receive the prosthesis, or phantom prosthesis, which is to be inserted.

It will be appreciated that the outer diameter of the elongate body portion will be appropriate for the prosthesis with which it is to be used.

The construction is such that the trephine can be easily dismantled for cleaning. Thus, it is merely necessary to remove the stop 18 so that the piston can slide out of the bore 11. Similarly the operating handle 17 is screw threaded onto the proximal end of the body portion 10 so that it can also be easily removed. The construction can be such that a number of body portions of different external diameters can be provided but with a bore of a single diameter so that the piston can be used with other body portions, as can the handle 17. Alternatively, a series of devices can be provided for different diameters.

One of the advantages of the piston is that it can be used to clean the bore 11 during use and because of the stops it reduces the possibility of jamming bone chips in the bore 11 if a surgeon continues to operate the device with the bore full.

While there have been described and illustrated a surgical trephine, it will be apparent to those skilled in the art that variations and modifications are possible without deviating from the broad spirit and principle of the present invention which shall be limited solely by the scope of the claims appended hereto.

What is claimed is:

1. The method for using a surgical trephine in forming a cavity in the medullary canal of a femur comprising:

inserting a guide wire into the medullary canal;

inserting a trephine having a distal end, a proximal, and a hollow tubular portion over the guide wire, the trephine including a bore with cutting teeth formed around an annular end surface of said bore, the hollow tubular portion including a piston, said piston having a cannulation for slidably receiving the guide wire;

rotating the trephine to cut a cavity in the canal;

limiting the movement of the piston with respect to said hollow tubular portion by providing a stop on an inner surface of the bore for engaging a stop on said piston to prevent the disassembly of said piston from said trephine; and removing material cut from the canal from the trephine by removing said trephine from the canal and activating said piston to force material within the hollow tubular portion from the annular end of said bore.

2. The method for using a surgical trephine as set forth in claim 1, wherein the piston is a rod slidably received in said bore and includes a stop at a proximal end to prevent said piston from disengaging from said trephine.

3. The method for using a surgical trephine as set forth in claim 2, wherein said stop on said piston is a stop on said rod for limiting the movement of said rod within said bore in a distal to proximal direction within said hollow tubular portion.

4. The method for using a surgical trephine as set forth in claim 3, wherein the piston is moved from said distal end of said trephine towards said proximal end by the force of accumulated bone chips.

5. A surgical trephine adapted for boring an opening in the tamped bone chips comprising a distal end and a hollow elongate body portion having an internal bore, a stop extending from said body portion into said bore, the distal end has an annular cutting rim, a piston located in said bore with a piston surface facing towards said cutting rim, said piston movable in the bore, said piston having a stop for engaging the stop on the inner bore for limiting movement of the piston in the bore in a direction away from the distal end.

6. The surgical trephine as claimed in claim 5 in which said body portion includes an aperture in the wall passing into the bore at a point spaced away from the distal end to facilitate cleaning after operation.

7. The surgical trephine as claimed in claim 6 in which an extension or extended portion of the piston projects beyond a proximal end of the hollow body portion.

8. The surgical trephine as claimed in claim 7 in which said stop on the inner bore is provided for limiting the movement of the piston up said bore and away from the distal end to a piston adjacent the proximal end of said aperture.

9. The surgical trephine as claimed in claim 7 in which a proximal end of the extended portion of the piston or an extension thereof is provided with a removable stop means to limit the movement of the piston in a distal direction.

10. The surgical trephine as claimed in claim 5 in which said annular cutting rim is provided with cutting teeth.

11. The surgical trephine as claimed in claim 5 in which the hollow elongate body portion is provided with an operating handle.

12. The surgical trephine as claimed in claim 5 in which said elongate body portion is provided with a depth gauge.

13. The surgical trephine as claimed in claim 5 in which a gauge is provided on the extended portion of the piston, or extension thereof, to provide a position indicator.

14. The surgical trephine as claimed in claim 7 in which a proximal end of the extended portion of the piston or an extension thereof is provided with a coupling for attaching a power source so that the device can be operated by a power device.

15. The surgical trephine as claimed in claim 5 in which the piston is provided with means to accept a guide wire.

16. A surgical cutting instrument for cutting a bore in a bone comprising:
- an elongate tubular body having a wall surrounding an internal bore and an annular open end;
- a cutting element formed around said annular open end;
- a piston having a stop thereon slidably received within said bore;
- a piston actuator coupled to said piston for moving said piston towards said open end of said tubular body; and
- a stop extending from said wall into said bore for engaging said stop on the piston to limit the movement of the piston away from the open end of said tubular body.

17. The surgical trephine as claimed in claim 16 wherein said tubular body has an aperture formed in said wall adjacent said open end.

18. The surgical trephine as claimed in claim 17 in which the stop extending from said wall is provided for limiting the movement of the piston in said bore in a direction away from the open end to a position adjacent an end of said aperture furthest from said open end.

19. The surgical trephine as claimed in claim 16 in which the piston is provided with a removable stop means to limit the movement of the piston towards said open end.

20. The surgical trephine as claimed in claim 16 in which the piston is provided with means to accept a guide wire.

* * * * *

UNITED STATES PATENT AND TRADEMARK OFFICE
CERTIFICATE OF CORRECTION

PATENT NO. : 6,200,319 B1
DATED : March 13, 2001
INVENTOR(S) : Storer et al.

It is certified that error appears in the above-identified patent and that said Letters Patent is hereby corrected as shown below:

Column 2,
Line 54, after "used" insert -- , --.
Line 55, after "however" insert -- , --.
Line 56, after "techniques" insert -- , --.

Column 3,
Line 7, cancel "of".
Line 13, after "acts" insert -- as --.
Line 22, "11" should read -- 11' --.
Line 43, "14" should read -- 14' --.

Column 4,
Line 17, "have" should read -- has --.
Line 24, "The" should read -- A --.
Line 27, after "proximal" insert -- end --.

Column 5,
Line 11, "a" should read -- the --.

Signed and Sealed this

Ninth Day of October, 2001

Attest:

*Nicholas P. Godici*

NICHOLAS P. GODICI
*Attesting Officer*   *Acting Director of the United States Patent and Trademark Office*